US012605474B2

(12) United States Patent
Wilds et al.

(10) Patent No.: US 12,605,474 B2
(45) Date of Patent: Apr. 21, 2026

(54) METAL WORKING FLUID DECONTAMINATION APPARATUS

(71) Applicants:Ivan Mark Wilds, Nelson (GB); Paul Rodger Gerald Wilds, Nelson (GB)

(72) Inventors: Ivan Mark Wilds, Nelson (GB); Paul Rodger Gerald Wilds, Nelson (GB)

( * ) Notice: Subject to any disclaimer, the term of this patent is extended or adjusted under 35 U.S.C. 154(b) by 1355 days.

(21) Appl. No.: 17/594,929

(22) PCT Filed: May 3, 2019

(86) PCT No.: PCT/EP2019/061467
§ 371 (c)(1),
(2) Date: Nov. 3, 2021

(87) PCT Pub. No.: WO2019/211481
PCT Pub. Date: Nov. 7, 2019

(65) Prior Publication Data
US 2022/0211888 A1     Jul. 7, 2022

(30) Foreign Application Priority Data

May 3, 2018    (GB) ..................................... 1807281

(51) Int. Cl.
*A61L 2/02*          (2006.01)
*A61L 2/022*         (2026.01)
(Continued)

(52) U.S. Cl.
CPC ................. *A61L 2/022* (2013.01); *A61L 2/10* (2013.01); *A61L 2/26* (2013.01); *B01D 36/02* (2013.01);
(Continued)

(58) Field of Classification Search
CPC .......... C02F 1/008; C02F 1/325; C02F 1/004; C02F 1/66; C02F 1/001; C02F 1/00;
(Continued)

(56) References Cited

U.S. PATENT DOCUMENTS 5,137,654 A * 8/1992 Burke .................. B01D 61/145
                                                        516/53
5,158,677 A * 10/1992 Hewitt ................... B01D 17/00
                                                        210/776

(Continued)

FOREIGN PATENT DOCUMENTS

DE          2656362 A1    6/1978
KR       20170114475 A   10/2017
WO          03029154 A1    4/2003

OTHER PUBLICATIONS

International Search Report and Written Opinion for International Application No. PCT/EP2019/061467 dated Jun. 8, 2019 from European Patent Office.

(Continued)

*Primary Examiner* — Akash K Varma
(74) *Attorney, Agent, or Firm* — Keusey & Associates, P.C.

(57) ABSTRACT

Metal working fluid decontamination apparatus (10) includes: an intake arrangement (40) for metal working fluid (42); a pump (16) for providing, in use, flow pressure to the metal working fluid (42); a decontaminator (50) for reducing contamination in the metal working fluid (42); and an outlet arrangement (34) for the metal working fluid. The metal working fluid (42) is a fully synthetic metal working fluid, which comprises water and a water soluble synthetic concentrate which does not comprise oil.

20 Claims, 2 Drawing Sheets

(51) Int. Cl.

| | |
|---|---|
| *A61L 2/10* | (2006.01) |
| *A61L 2/26* | (2006.01) |
| *B01D 36/02* | (2006.01) |
| *C02F 1/00* | (2023.01) |
| *C02F 9/00* | (2023.01) |
| *C09K 5/20* | (2006.01) |
| *C09K 15/00* | (2006.01) |
| *C10M 173/02* | (2006.01) |
| *C10M 177/00* | (2006.01) |
| *C11D 7/50* | (2006.01) |
| *C02F 1/32* | (2023.01) |
| *C02F 1/66* | (2023.01) |
| *C02F 103/16* | (2006.01) |
| *C10N 40/08* | (2006.01) |
| *C10N 40/22* | (2006.01) |
| *C10N 40/24* | (2006.01) |
| *C10N 70/00* | (2006.01) |

(52) U.S. Cl.

CPC ............... *C02F 1/008* (2013.01); *C02F 9/00* (2013.01); *C09K 5/20* (2013.01); *C09K 15/00* (2013.01); *C10M 173/02* (2013.01); *C10M 177/00* (2013.01); *C11D 7/50* (2013.01); *A61L 2202/11* (2013.01); *A61L 2202/14* (2013.01); *C02F 1/004* (2013.01); *C02F 1/325* (2013.01); *C02F 1/66* (2013.01); *C02F 2103/16* (2013.01); *C02F 2201/006* (2013.01); *C02F 2201/3227* (2013.01); *C02F 2201/328* (2013.01); *C02F 2209/001* (2013.01); *C02F 2209/003* (2013.01); *C02F 2209/03* (2013.01); *C02F 2209/06* (2013.01); *C02F 2301/024* (2013.01); *C02F 2301/043* (2013.01); *C02F 2301/08* (2013.01); *C02F 2303/04* (2013.01); *C10N 2040/08* (2013.01); *C10N 2040/22* (2013.01); *C10N 2040/24* (2013.01); *C10N 2070/00* (2013.01)

(58) Field of Classification Search

CPC .... C02F 1/32; C02F 1/444; C02F 9/00; C02F 2103/16; C02F 2201/006; C02F 2201/3227; C02F 2201/328; C02F 2201/322; C02F 2209/001; C02F 2209/003; C02F 2209/03; C02F 2209/06; C02F 2301/024; C02F 2301/043; C02F 2301/08; C02F 2303/04; B01D 36/02; B01D 35/02; B01D 37/00; B01D 2221/14; B01D 61/14; B01D 61/18; B01D 61/22; C09K 5/20; C09K 15/00; C10M 173/02; C10M 173/00; C10M 175/00; C10M 175/0058; C10M 175/0066; C10M 177/00; C11D 7/50; C10N 2040/08; C10N 2040/22; C10N 2040/24; C10N 2070/00; A61L 2/022; A61L 2/10; A61L 2/26; A61L 2/02; A61L 2202/11; A61L 2202/14; A61L 2202/17; Y02A 20/152; Y02A 20/156; Y02P 70/20

USPC ........................................ 210/741

See application file for complete search history.

(56) References Cited

U.S. PATENT DOCUMENTS

| | | | | |
|---|---|---|---|---|
| 5,447,642 | A | * | 9/1995 | Schenach .................. C02F 9/00 210/167.04 |
| 5,552,040 | A | * | 9/1996 | Baehler ............ C10M 175/0058 210/167.04 |
| 5,997,812 | A | * | 12/1999 | Burnham .................. C02F 1/48 210/695 |
| 6,083,387 | A | * | 7/2000 | LeBlanc ................... C02F 1/48 422/186.3 |
| 6,464,936 | B1 | | 10/2002 | Mowat |
| 2004/0226887 | A1 | * | 11/2004 | Rajagopalan ........ C10M 175/04 210/791 |
| 2008/0102005 | A1 | * | 5/2008 | Messier ............... C10M 173/02 422/281 |
| 2011/0240564 | A1 | * | 10/2011 | Mueller ................... B63J 4/002 210/748.1 |
| 2016/0053425 | A1 | * | 2/2016 | Wolff ................... B01D 71/024 68/10 |

OTHER PUBLICATIONS

CIMCOOL Technical Report, Waterbased Metalworking Fluids: Proper Mixing Practices, Milicron Marketing Technical Report, 2005.

* cited by examiner

METAL WORKING FLUID DECONTAMINATION APPARATUS

BACKGROUND OF THE INVENTION

1. Field of the Invention

The present invention relates to metal working fluid decontamination apparatus.

2. The Prior Art

Metal working fluids are fluids which are used to lubricate and/or cool metal work pieces in metal working operations such as machining, cutting and forming.

Conventionally, metal working fluids are formed by adding a concentrate to water. The most commonly used concentrates comprise oil and performance additives including an emulsifier, and when added to water form a semi translucent or milky white emulsion.

One alternative to a conventional metal working fluid is a fully synthetic metal working fluid, which comprises water and a water soluble synthetic concentrate which does not contain oil. Examples of fully synthetic metal working fluids include water-miscible metal working fluids.

In use, a tank of the metal working fluid is located on or close by to the machine performing the metal working operation. The metal working fluid is pumped from the tank to the workpiece. After lubricating and/or cooling the work piece during the metal working operation, the metal working fluid is collected and conveyed back to the tank. Over a period of time, the metal working fluid becomes contaminated by a range of contaminants, including metal particulates, air borne particulates, tramp oil and microbial contaminants such as bacteria. The contaminants present a risk to the health of the machine operatives and also reduce the effectiveness of the metal working fluid.

In practice, microbial contamination is of most concern, as it presents a serious health risk, and causes unpleasant odours. Water-miscible metal working fluids (MWFs) by their nature become colonised by bacteria living in the environment if not maintained properly. The majority of MWFs adapted bacteria belong to the *Pseudomonas* family and are Gram negative meaning their surface consists of a double surface membrane. Bacteria die off naturally due to limited availability of nutrients in the MWF and are killed by the addition of biocide and other additives in an endeavour to manage the MWF quality. Once cell death occurs, the outer surface membrane breaks down releasing immunologically active proteins and potential toxins into the MWF. The main one of concern, due to its known link to respiratory ill health, is endotoxin. Thus, microbial contamination results in poor and potentially unsafe working conditions for the operatives.

Conventionally, metal working fluid contamination requires that metal working fluids are replaced on a regular, periodic basis as they become contaminated, entailing disposal costs for the user. To extend the period of use before replacement, biocides are used to prevent or reduce the growth of bacteria. However, the biocides become depleted over time and increased use of biocides itself presents a health, safety and environmental concern. In addition, regulatory changes may limit the availability of biocides as tank side additives.

In this specification, the term "metal working fluid" is used to include fluids which are used in relation to metal working machinery, including cutting fluids, grinding fluids, drawing and forming fluids, coolants, component cleaners, press lubricants, corrosion inhibitors and degreasers.

In this specification, the term "micron" is used and means $1 \times 10\text{-}6$ m. Filters are commonly rated in microns. The rating relates to the size of the holes in the filter and thus the size of the particles which are trapped by the filter. Thus, a 50 micron filter traps particles of 50 microns or larger, while a 2 micron filter traps particles of two microns or larger. Filters can be further classified as "nominal" or "absolute." A nominal 5 micron filter is one that traps 85 percent of particles of 5 microns and larger, while a 5 micron absolute rated filter will remove at least 98.7% of particles of 5 microns or larger. Bacteria range in size from 0.2 to 2 microns in width or diameter and from 1 to 10 microns in length for non-spherical specie. *Pseudomonas* bacteria is rod shaped, the rod being about 1 to 5 microns long and 0.5 to 1.0 micron wide. Thus, a 1-micron filter will remove most bacteria and cysts but only a proportion of *pseudomonas*, while a 0.1 micron filter will remove substantially all bacteria, including *pseudomonas*.

In this specification, all of the filter ratings given are absolute filter ratings unless otherwise stated.

For the avoidance of doubt, in this specification, the term "at least a 20 micron filter" (or similar) means that the filter will filter out particulates at least down to 20 microns, and the term "no more than a 1.0 micron filter" (or similar) means that the filter does not filter out particulates below 1.0 micron (with the actual micron values adjusted accordingly as the reader will understand).

SUMMARY OF THE INVENTION

According to a first aspect of the present invention, there is provided metal working fluid decontamination apparatus, the apparatus including:

an intake arrangement for metal working fluid;

a pump for providing, in use, flow pressure to the metal working fluid;

a decontaminator for reducing contamination in the metal working fluid;

an outlet arrangement for the metal working fluid;

whereby, the metal working fluid is a fully synthetic metal working fluid, which comprises water and a water soluble synthetic concentrate which does not comprise oil.

Possibly, the metal working fluid comprises, in a fresh (i.e. unused) condition, no more than 10% by weight of the synthetic concentrate, and may comprise no less than 2% by weight of the synthetic concentrate in the fresh condition. Desirably, the metal working fluid comprises, in the fresh condition, no more than 7% by weight of the synthetic concentrate, and may comprise no less than 5% by weight of the synthetic concentrate.

Possibly, the metal working fluid is, in the fresh condition, substantially transparent.

Possibly, the decontaminator comprises a filter arrangement, to reduce particulate contamination in the metal working fluid.

Possibly, the filter arrangement comprises a coarse filter for filtering particulates. Possibly, the coarse filter is at least a 20 micron filter, and may be no more than a 5 micron filter.

Possibly, the filter arrangement comprises a fine filter for filtering particulates. Possibly, the fine filter is at least a 20 micron filter, and may be no more than a 0.5 micron filter.

Possibly, the filter arrangement comprises a microbial filter for filtering microbial particulates, such as bacteria. Possibly, the microbial filter is positively charged. Possibly, the microbial filter is at least a 1.0 micron filter and may be no more than a 0.1 micron filter.

Possibly, the filter arrangement comprises the coarse filter, the fine filter, and the microbial filter in flow sequence.

Possibly, the apparatus comprises pressure gauges, which may be located upstream and downstream of the or each filter, possibly to indicate the pressure drop over each filter and thereby whether any of the filters need replacing.

Possibly, the decontaminator comprises an ultraviolet (UV) light treatment arrangement, possibly to reduce microbial contamination and possibly to reduce endotoxins in the metal working fluid.

Possibly, the UV light treatment arrangement defines a treatment passage along which, in use, the metal working fluid flows. Possibly, the arrangement includes a UV light source which is arranged to treat the metal working fluid as it flows along the passage.

Possibly, the UV light source operates at a wavelength of 185 to 400 nm.

Possibly, the UV light source comprises a low pressure UV light source, which may operate at a wavelength of 185 to 254 nm, and/or may comprise a medium pressure UV light source, which may operate at a wavelength of 200 to 400 nm.

Possibly, the UV light treatment arrangement includes passage walling, which may define the treatment passage. Possibly, the passage walling is substantially transparent, and may be formed of glass, possibly, quartz.

Possibly, the UV light treatment arrangement includes at least four UV light sources, which may be arranged around the passage walling, and may be equally spaced around the passage walling.

Possibly, the UV light treatment arrangement is arranged so that the, or one, or some, or each of the UV light sources is located within the treatment passage, so that, in use, the metal working fluid flows around the UV light source(s). Possibly, the UV light source(s) is (are) located within the passage walling, possibly on the inside of the passage walling, and, in use, the metal working fluid flows around the outside of the passage walling.

Possibly, the UV light treatment arrangement includes a flow disrupter, which, in use, alters the flow of the metal working fluid along the passage from laminar flow to turbulent flow. Possibly, the flow disrupter includes one or more static mixing elements.

Possibly, the apparatus includes a pH monitor, for monitoring the pH of the metal working fluid. Possibly, the pH monitor includes a detector, for detecting the pH of the metal working fluid. Possibly, the pH monitor includes a display, for displaying the pH of the metal working fluid.

Possibly, the apparatus includes a controller, which may include a display. Possibly, the pH monitor is in signal communication with the controller, possibly by wire or wirelessly.

Possibly, the pH monitor includes a logger, for recording the pH of the metal working fluid. Possibly, the pH monitor includes a transmitter, for transmitting the pH of the metal working fluid to a remote display and/or a remote logger or to the controller.

Possibly, the pH monitor is located downstream of the decontaminator.

Possibly, the pH monitor is located upstream of the decontaminator.

Possibly, the apparatus includes a plurality of pH monitors. Possibly, one monitor is located upstream of the decontaminator, and one monitor is located downstream of the decontaminator.

Possibly, the apparatus includes a pH adjuster, for adjusting the pH of the metal working fluid. Possibly, the pH adjuster is located in flow sequence after the decontaminator. Possibly, the pH adjuster includes a pH monitor for monitoring the pH of the metal working fluid. Possibly, the pH adjuster includes a dosing pump for dosing a pH adjustment fluid into the metal working fluid, to adjust the pH of the metal working fluid. Possibly, the pH adjuster includes a controller, which, in use, may control the operation of the dosing pump in accordance with the level of pH detected in comparison with a predetermined desired level of pH.

Possibly, the pH adjustment fluid comprises a pH raising fluid.

Possibly, the predetermined desired pH level is in the range 8.6-9.1.

Possibly, the intake arrangement includes a strainer, for straining out relatively large particles, such as metal swarf.

Possibly, the intake arrangement includes a suction tube, which may be located in or attached to a tank of metal working fluid.

Possibly, the outlet arrangement includes an outlet tube, which may be located in or attached to the tank of metal working fluid.

Possibly, the decontaminator includes a bypass flow line, to permit the metal working fluid to bypass the UV light treatment arrangement. Possibly, the decontaminator includes a bypass control valve arrangement for switching flow of the metal working fluid between a treatment condition, in which the metal working fluid flows through the UV light treatment arrangement, and a bypass condition, in which the metal working fluid flows through the bypass flow line.

Possibly, the decontaminator includes a pH monitor, for monitoring the pH of the metal working fluid. Possibly, the pH monitor is located upstream of the UV light treatment arrangement and may be located between the UV light treatment arrangement and the filter arrangement.

Possibly, the decontaminator includes a bypass controller which receives a pH signal from the decontaminator pH monitor.

Possibly, the bypass controller sends control signals to the bypass control valve arrangement to switch the flow between the treatment condition and the bypass condition. Possibly, the switching is dependent on the monitored value of the pH at the decontaminator pH monitor relative to a predetermined pH control value.

Possibly, if the monitored value of the pH matches or exceeds the predetermined pH control value, the bypass controller sends a control signal to the bypass control valve arrangement to switch the flow from the treatment condition to the bypass condition.

Possibly, if the monitored value of the pH is lower than the predetermined pH control value, the bypass controller sends a control signal to the bypass control valve arrangement to switch the flow from the bypass condition to the treatment condition.

Possibly, the predetermined pH control value is 8.5.

Possibly, the metal working fluid does not comprise a bactericide.

Possibly, the metal working fluid is for use as one or more of a cutting fluid, a grinding fluid, a drawing and/or forming fluid, a coolant, a component cleaner, a press lubricant, a corrosion inhibitor and/or a degreaser.

According to a second aspect of the present invention, there is provided method of decontaminating metal working fluid, the method including providing metal working fluid decontamination apparatus, the apparatus including:

an intake arrangement for metal working fluid;

a pump for providing, in use, flow pressure to the metal working fluid;

a decontaminator for reducing contamination in the metal working fluid;

an outlet arrangement for the metal working fluid;

whereby, the metal working fluid is a fully synthetic metal working fluid, which comprises water and a water soluble synthetic concentrate which does not contain oil.

Possibly, the apparatus includes any of the features described in any of the preceding statements or following description. Possibly, the method includes any of the steps described in any of the preceding statements or following description.

BRIEF DESCRIPTION OF THE DRAWINGS

Embodiments of the present invention will now be described, by way of example only, and with reference to the accompanying drawings, in which:—

DETAILED DESCRIPTION OF THE PREFERRED EMBODIMENTS

Figures 1, 2:
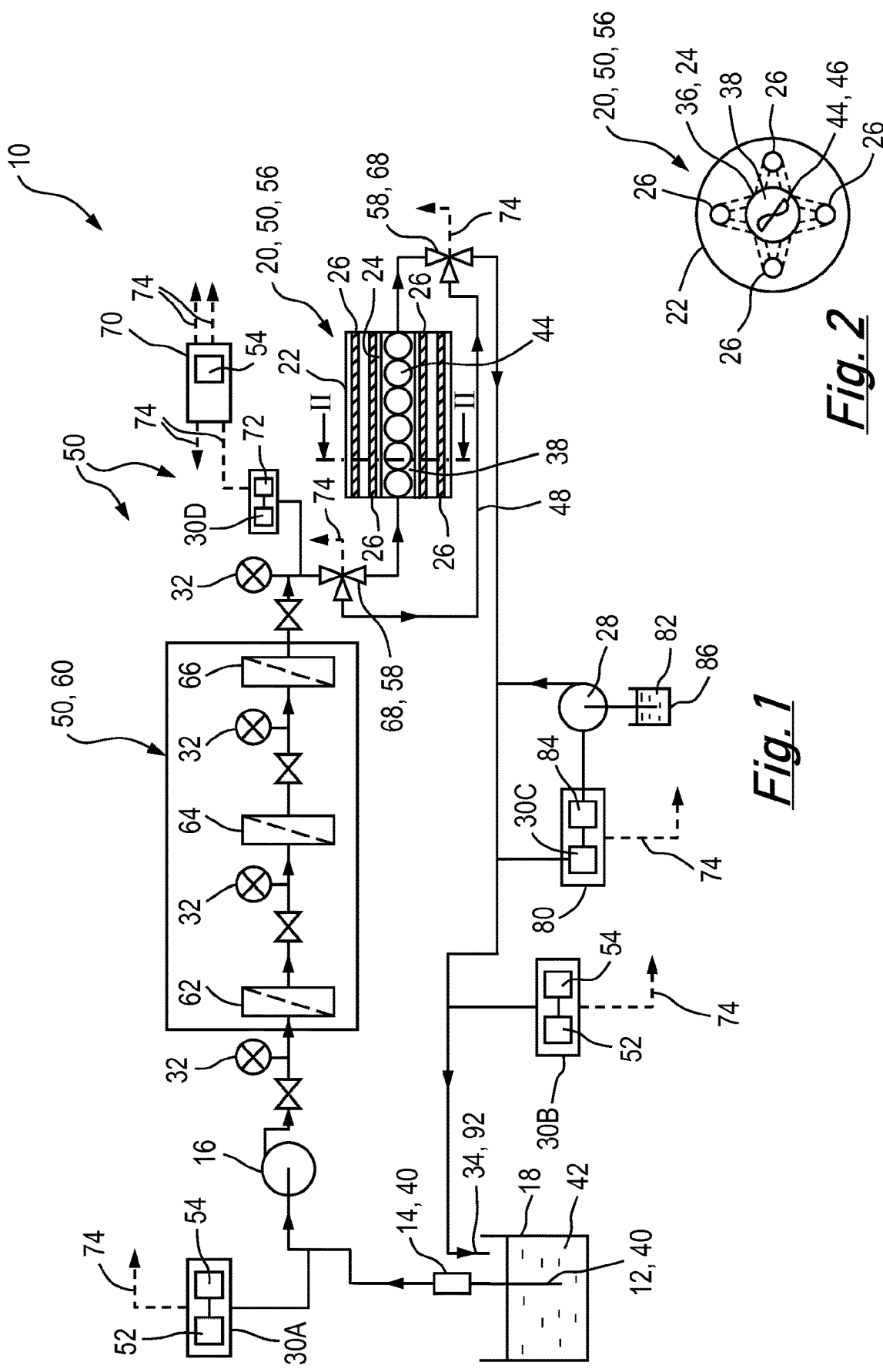
FIG. 1 is a schematic view of metal working fluid decontamination apparatus.
FIG. 2 is a sectional schematic view through a UV light treatment arrangement of the apparatus of FIG. 1 as indicated by arrows II-II in FIG. 1.

FIGS. 1 and 2 show metal working fluid decontamination apparatus 10. The apparatus 10 includes: an intake arrangement 40 for metal working fluid 42; a pump 16 for providing, in use, flow pressure to the metal working fluid 42; a decontaminator 50 for reducing contamination in the metal working fluid 42; and an outlet arrangement 34 for the metal working fluid.

The metal working fluid 42 is a fully synthetic metal working fluid, which comprises water and a water soluble synthetic concentrate which does not comprise oil. The metal working fluid 42 is non-combustible.

In one example, the metal working fluid 42 could comprise, in a fresh (i.e. unused) condition, no more than 10% by weight of the synthetic concentrate, and could comprise no less than 2% by weight of the synthetic concentrate in the fresh condition. In another example, the metal working fluid 42 could comprise, in the fresh condition, no more than 7% by weight of the synthetic concentrate, and could comprise no less than 5% by weight of the synthetic concentrate.

The metal working fluid 42 is, in the fresh condition, substantially transparent.

In one example, the pump 16 could be a self-priming centrifugal pump. In other examples, the pump 16 could be a positive displacement pump.

The decontaminator 50 comprises a filter arrangement 60, to reduce particulate contamination in the metal working fluid 42.

The filter arrangement 60 comprises a coarse filter 62 for filtering particulates. In one example, the coarse filter 62 could be at least a 20 micron filter (i.e. filters out particulates at least down to 20 microns), and could be no more than a 5 micron filter (i.e. does not filter out particulates below 5 microns).

The filter arrangement 60 comprises a fine filter 64 for filtering particulates. In one example, the fine filter 64 is at least a 20 micron filter (i.e. filters out particulates at least down to 20 microns), and could be no more than a 0.5 micron filter (i.e. does not filter out particulates below 0.5 microns).

The filter arrangement 60 comprises a positively charged microbial filter 66 for filtering microscopic particulates, which could include metal particles such as brass and microbial particles such as bacteria. In one example, the microbial filter 66 could be at least a 1.0 micron filter (i.e. filters out particulates at least down to 1.0 micron), and could be no more than a 0.1 micron filter (i.e. does not filter out particulates below 0.1 micron).

In the example shown, the filter arrangement 60 comprises the coarse filter 62, the fine filter 64, and the microbial filter 66 in flow sequence.

All of the filters 62, 64, 66 could comprise replaceable filter cartridges or filter bags.

The apparatus 10 comprises pressure gauges 32 which are located upstream and downstream of each of the filters 62, 64, 66, to indicate the pressure drop over each filter 62, 64, 66 and thereby whether any of the filters 62, 64, 66 need replacing.

The decontaminator 50 comprises an ultraviolet (UV) light treatment arrangement 20, to reduce microbial contamination and endotoxins in the metal working fluid 42.

The UV light treatment arrangement 20 defines a treatment passage 38 along which, in use, the metal working fluid 42 flows. The arrangement 20 includes a UV light source 26 which is arranged to treat the metal working fluid 42 as it flows along the passage 38.

In one example, the UV light source 26 operates at a wavelength of 185 to 400 nm. The UV light source 26 could comprise a low pressure UV light source, which could operate at a wavelength of 185 to 254 nm, and/or could comprise a medium pressure UV light source, which could operate at a wavelength of 200 to 400 nm.

The UV light treatment arrangement 20 includes a UV light treatment unit 56 which includes passage walling 36 which defines the treatment passage 38. In the example shown, the passage walling 36 is in the form of a tube 24. The passage walling 36 is substantially transparent, and could be formed of glass. In one example, the passage walling 36 is formed of quartz. In the example shown, the unit 56 includes four UV light sources 26, which are equispaced around the passage walling 36 to provide even 360° illumination of the passage walling 36 and which treat the metal working fluid 42 as it flows along the passage 38.

The UV light treatment unit 56 includes a housing 22, in which the UV light sources 26 and the passage walling 36 are located, and which could be formed of a corrosion resistant metal such as stainless steel or aluminium.

The UV light treatment unit 56 includes a flow disrupter 44, which is located in the passage 38 and, in use, alters the flow of the metal working fluid 42 along the passage 38 from laminar flow to turbulent flow. The flow disrupter 44 includes one or more static mixing elements 46, which could be spiral type plastic elements.

In one example, the length of the passage 38 is approximately 800-1200 mm and the diameter is 20 mm. The flow rate of metal working fluid 42 is approximately 20 to 40 l/min and the energy consumed is 75-400 W.

The apparatus 10 includes a plurality of pH monitors 30A, 30B for monitoring the pH of the metal working fluid 42. Each pH monitor 30A, 30B includes a detector 52, for detecting the pH of the metal working fluid 42 and could include a local display 54, for displaying the pH of the metal working fluid 42.

The apparatus 10 could include a controller 70, which could include a local display 54. Each of the pH monitors 30A, 30B could be in signal communication with the controller 70, either by wire or wirelessly, as indicated by partial dashed lines 74.

In the example shown, one pH monitor 30A is located upstream of the decontaminator 50 and another pH monitor 30B is located downstream of the decontaminator 50. This permits monitoring of the alkalinity levels of the metal working fluid 42 before and after passing through the decontaminator 50.

The apparatus includes a pH adjuster 80, for adjusting the pH of the metal working fluid 42. The pH adjuster 80 is located in flow sequence after the decontaminator 50. In one example, the pH adjuster 80 includes a pH monitor 30C for monitoring the pH of the metal working fluid 42. The pH adjuster 80 includes a dosing pump 28 for dosing a pH adjustment fluid 82 (which could be stored in a container 86) into the metal working fluid 42, to adjust the pH of the metal working fluid 42.

In the example shown, the pH adjuster 80 includes a controller 84, which, in use, controls the operation of the dosing pump 28 in accordance with the level of pH detected by the monitor 30C, in comparison with a predetermined desired level of pH.

The pH adjustment fluid 82 comprises a pH raising fluid.

In some examples, the detector 52 of the downstream pH monitor 30B could comprise the monitor 30C of the pH adjuster 80.

In some examples, the monitor 30C and/or the controller 84 of the pH adjuster 80 could comprise, or be in signal communication with, the controller 70, either by wire or wirelessly, as indicated by partial dashed lines 74.

The intake arrangement 40 includes a strainer 14, for straining out relatively large particles, such as metal swarf. The intake arrangement 40 includes a suction tube 12, which could be located in or attached to a tank 18 of the metal working fluid 42.

The outlet arrangement 34 includes an outlet tube 92, which could be located in or attached to the tank 18 of the metal working fluid 42.

The decontaminator 50 includes a bypass flow line 48, to permit the metal working fluid 42 to bypass the UV light treatment unit 56. The decontaminator 50 includes a bypass control valve arrangement 58 for switching flow of the metal working fluid 42 between a treatment condition, in which the metal working fluid 42 flows through the UV light treatment unit 56 and a bypass condition, in which the metal working fluid 42 flows through the bypass flow line 48.

The decontaminator 50 includes a decontaminator pH monitor 30D, for monitoring the pH of the metal working fluid 42. The decontaminator pH monitor 30D is located upstream of the UV light treatment unit 56, between the UV light treatment unit 56 and the filter arrangement 60.

The decontaminator 50 includes a bypass controller 72 which receives a pH signal from the decontaminator pH monitor 30D.

The bypass controller 72 sends control signals to the bypass control valve arrangement 58 to switch the flow between the treatment condition and the bypass condition, dependent on the monitored value of the pH at the decontaminator pH monitor 30D relative to a predetermined control value.

In some examples, the bypass controller 72 could comprise, or be in signal communication with, the controller 70, either by wire or wirelessly, as indicated by partial dashed lines 74.

The metal working fluid 42 could be for use as one or more of a cutting fluid, a grinding fluid, a drawing and/or forming fluid, a coolant, a component cleaner, a press lubricant, a corrosion inhibitor and/or a degreaser.

In Use

In use, the pump 16 is operated and draws the metal working fluid 42 from the machine tank 18 into the suction tube 12. In a contaminated condition, from the machine tank 18, the metal working fluid 42 is usually opaque.

The metal working fluid 42 flows through the strainer 14 and through the three stage filter arrangement 60 of the coarse filter 62, the fine filter 64 and the microbial filter 66.

After filtration, the metal working fluid 42 is substantially transparent.

The decontaminator pH monitor 30D monitors the pH value of the metal working fluid 42 exiting the filter arrangement 60. The bypass controller 72 compares the monitored value of the pH at the decontaminator pH monitor 30D relative to a predetermined control value.

If the monitored value of the pH matches or exceeds the predetermined pH control value, the bypass controller 72 sends a control signal to the bypass control valve arrangement 58 to switch the flow from the treatment condition to the bypass condition.

If the monitored value of the pH is lower than the predetermined pH control value, the bypass controller 72 sends a control signal to the bypass control valve arrangement 58 to switch the flow from the bypass condition to the treatment condition.

In one example, the predetermined pH control value is 8.5.

In the treatment condition, the metal working fluid 42 flows through the UV light treatment unit 56. As it does so, UV light from the UV light sources 26 illuminates the metal working fluid 42 to kill bacteria therein. The static mixing elements 46 of the flow disrupter 44 ensure the flow is turbulent flow to provide thorough treatment.

If the monitored value of the pH is higher than the predetermined pH control value (eg higher than 8.5), the bypass controller 72 sends a control signal to the bypass control valve arrangement 58 to switch the flow from the treatment condition to the bypass condition and the metal working fluid 42 does not pass through the UV light treatment unit 56. In the bypass condition, the UV light treatment unit 56 can be switched off to save power.

The pH of the decontaminated metal working fluid 42 is monitored by the pH adjuster 80. If the pH is below the predetermined desired level, the pH adjuster controller 84 operates the dosing pump 28 which doses the pH raising fluid 82 into the metal working fluid 42 to raise the pH of the metal working fluid 42. The pH raising fluid 82 does not comprise a biocide.

In one example, the predetermined desired pH level is in the range 8.6-9.1.

The decontaminated and pH adjusted metal working fluid 42 then flows back to the machine tank 18.

Upstream and downstream pH monitors 30A, 30B provide indication of the pH of the metal working fluid 42 before and after treatment.

In one example, the bacterial load in the metal working fluid 42 before treatment could be 106 CFU/ml (colony forming units per ml). After a period of treatment using the apparatus 10, the Applicant has found that the bacterial load could be reduced to 103 CFU/ml.

The Applicant has realised that one of the properties of fully synthetic metal working fluids, namely transparency, can be utilised to permit UV light treatment. Conventionally, UV light treatment of metal working fluids has been unsuccessful, since most metal working fluids are usually emulsions with poor light transmission properties. Also, emulsifiers in the metal working fluid emulsify tramp oil from the machine which causes shadowing. Tests of emulsion metal working fluids have shown that penetration of UV light is 100% attenuated at 1 mm depth.

A further disadvantage of emulsion metal working fluids is that filtration is limited to no lower than 10 micron as anything smaller can remove emulsion particles such as additives and oil, effectively disrupting the stability of the emulsion.

The Applicant has realised that fully soluble synthetic metal working fluids permit the use of finer filters, which can be used to remove microbial particles such as bacteria.

The Applicant has surprisingly found that the three stage filtration of the apparatus 10 is effective in providing a satisfactorily treated metal working fluid without, or with reduced, use of biocide and without requiring UV treatment.

However, the filters are not 100% effective in removing all microbial particulate. Hence, the UV treatment arrangement provides a cleaner, safer metal working fluid 42 which results in safer working conditions for operators, and longer filter life.

A further benefit is reduced use of biocide, with attendant environmental benefits, particularly on disposal. In fact, the Applicant has found that use of the apparatus 10 means that bactericide or biocide use in the metal working fluid is not required or greatly reduced.

The Applicant has further realised that pH provides an indication of bacterial load. A higher bacterial load will result in a lowering of pH. Thus by measuring pH, a measure of the bacterial load of the metal working fluid 42 can be obtained and hence health and safety risk can be assessed. In the apparatus 10, this understanding is used to control flow through the UV light treatment unit 56. At satisfactory pH levels (i.e. low bacterial load) the flow of the metal working fluid 42 is diverted through the bypass line 48, thus saving energy.

Other Embodiments

Figure 4:
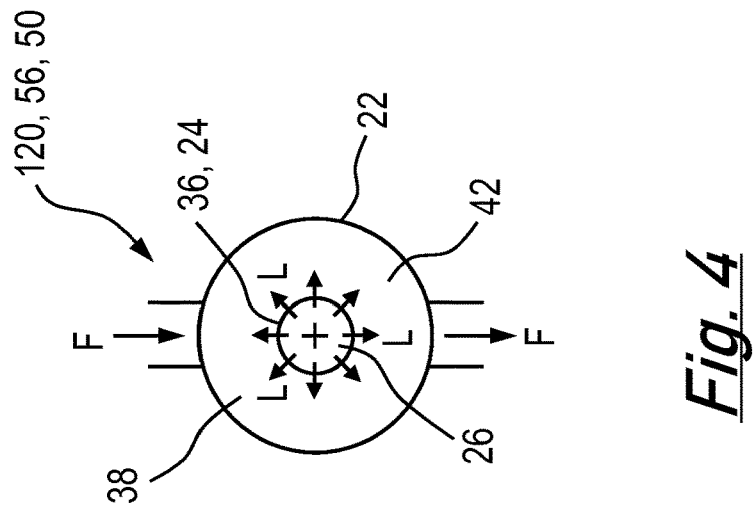
FIG. 4 is an end view of the UV light treatment arrangement of FIG. 3.
Figure 3:
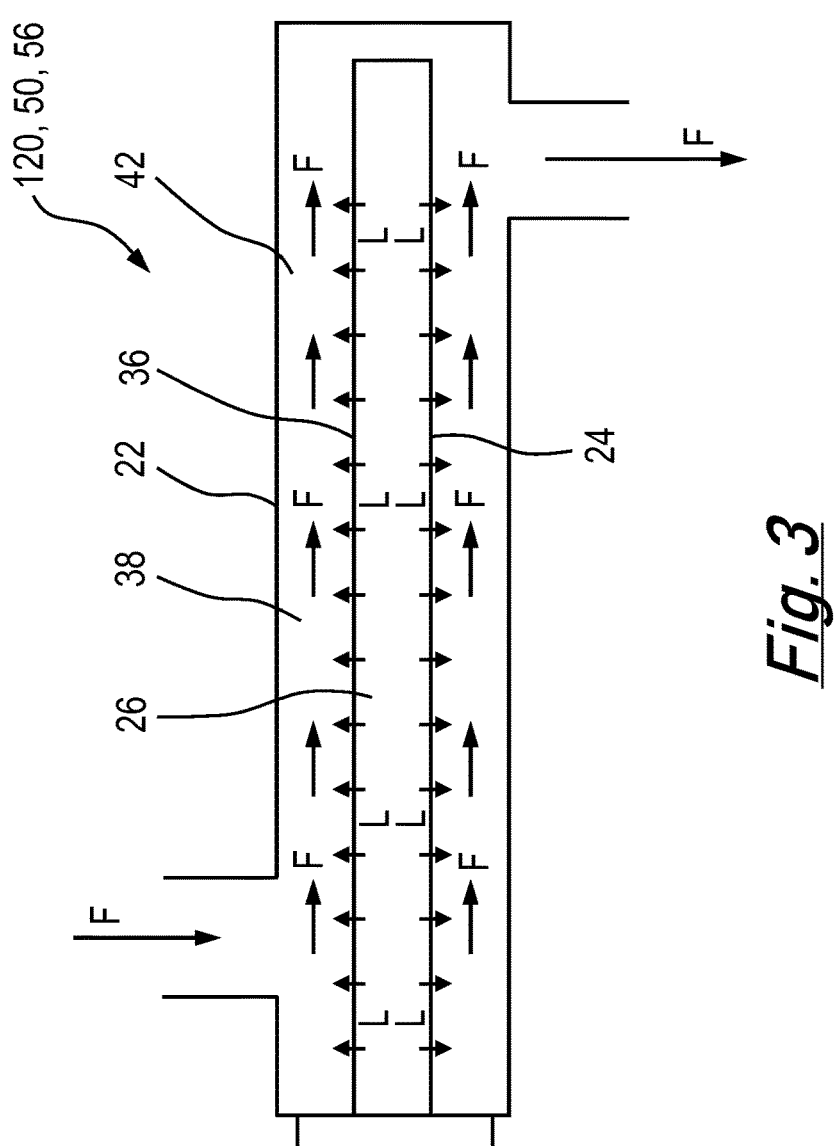
FIG. 3 is a sectional schematic view of another UV light treatment arrangement.

FIGS. 3 and 4 show another embodiment of the invention, many features of which are similar to those already described in relation to the embodiment of FIGS. 1 and 2. Therefore, for the sake of brevity, the following embodiment will only be described in so far as it differs from the embodiment already described. Where features are the same or similar, the same reference numerals have been used and the features will not be described again.

FIGS. 3 and 4 show another UV light treatment arrangement 120. The UV light treatment arrangement 120 includes a UV light treatment unit 56. The UV light treatment unit 56 includes a housing 22 and passage walling 36. The housing 22 and the passage walling 36 define a treatment passage 38 therebetween, along which, in use, the metal working fluid 42 flows. In the example shown, the passage walling 36 is in the form of a tube 24, which is circular in cross-section. The passage walling 36 is substantially transparent, and could be formed of glass. In one example, the passage walling 36 is formed of quartz.

In the example shown, the unit 56 includes a UV light source 26, which is located within the treatment passage 38, within the passage walling 36. In the example shown, the UV light source 26 is on the inside of the passage walling 36 and the metal working fluid 42 flows, in use, around the outside of the passage walling 36.

In FIGS. 3 and 4, arrows F indicate the flow of the metal working fluid 42 and arrows L indicate the direction of the UV light transmission. Thus, in use, the metal working fluid 42 flows into the unit 56 and along the unit 56, along the passage 38 between the housing 22 and the passage walling 36. UV light is transmitted outwardly from the UV light source 26 through the passage walling 36 to treat the metal working fluid 42 in the treatment passage 38. In this embodiment, the metal working fluid 42 flows around the UV light source 26, maximising the efficiency of the UV light treatment arrangement 120.

A flow disrupter 44 could be located in the treatment passage 38 as in the previous embodiment, or upstream thereof, to ensure the flow is turbulent and provide thorough treatment.

Other Modifications

Various other modifications could be made without departing from the scope of the invention. The apparatus and its various components could be of any suitable size and shape, and could be formed of any suitable material (within the scope of the specific definitions herein).

The apparatus 10 could be used to treat any mineral oil free cutting fluid or aqueous machine cleaner.

The apparatus 10 could be provided to be permanently fixed to a machine, built integrally into the machine (for example, as part of the machine filtration system) or temporarily connected to the machine.

If temporarily connected, (ie mobile) the apparatus 10 could be moved to different machines on a periodic basis.

If permanently fixed or integral, the apparatus 10 could be programmed to operate on a periodic basis eg a certain number of hours per day, and/or on certain days of the week or month.

If permanently fixed or integral, the coarse and fine filters 62, 64 of the apparatus 10 could be integrated into the machine filtration system.

The apparatus 10 could be used remote from the machine, to treat stored used metal working fluid. For example, the apparatus 10 could draw metal working fluid from one storage vessel (eg an Intermediate Bulk Container or IBC), and provide the decontaminated metal working fluid either back to the same IBC or to another IBC.

In another example, the apparatus 10 could include a pH monitor (not shown) which measures the pH in the machine tank 18 and the controller 70 could operate the apparatus 10 when the pH in the tank 18 falls below a predetermined level.

The intake arrangement 40 could include a coupling or connector, eg a camlock quick release connector (not shown), to connect to a fitting (not shown) on the tank 18. Similarly, the outlet arrangement 34 could include a coupling or connector, e.g. a camlock quick release connector (not shown), to connect to a fitting (not shown) on the tank 18.

The number of pH monitors could vary. The pH monitors could be standalone devices or linked to the controller or to another device. The or each or one or some of the pH monitors could include a logger, for recording the pH of the metal working fluid, and/or a transmitter, for transmitting the pH of the metal working fluid to a remote display and/or a remote logger or controller.

The apparatus 10 could include a different number of filters. The filters could be operated independently, so that the user can select which filters operate. For example, a bypass line could be provided for the microbial filter 66 and the pH of the metal working fluid 42 monitored at the exit of the fine filter 64. If the monitored value of the pH matches or exceeds the predetermined pH control value, then the metal working fluid 42 could be directed along the bypass line, extending the life of the microbial filter 66.

Any or all of the control valves, dosing pump and pH monitors could be manually operated.

The filters could be of any suitable type.

The UV light treatment arrangement could comprise any suitable number of UV light treatment units. The UV light treatment units could be of any suitable type and could comprise any suitable arrangement (including number, design and type) of passage walls, tubes, mixing elements and UV light sources, arranged in any suitable way. In one example, the UV light treatment arrangement could comprise a plurality of UV light treatment units which, could be arranged in parallel or, more desirably, in series.

In one example, the UV light source 26 could comprise both the low pressure UV light source operating at the wavelength of 185 to 254 nm, and the medium pressure UV light source, operating at a wavelength of 200 to 400 nm. The UV light sources 26 could be arranged in series.

Both the low pressure UV light source and the medium pressure UV light source operate to destroy bacteria (and hence reduce bacterial contamination) and oxidise endotoxins (and hence reduce toxicity). However, the Applicant has found evidence that the low pressure UV light source is more effective than the medium pressure UV light source in destroying bacteria, and the medium pressure UV light source is more effective than the low pressure UV light source in oxidising endotoxins. Ideally, therefore, the combination in series of both the low pressure UV light source and the medium pressure UV light source would appear to be most effective, but is relatively costly and requires a lot of space and therefore with the presently available technology can only be justified for large installations.

In one example, the flow disrupter could be located upstream of the treatment passage.

Any of the features or steps of any of the embodiments shown or described could be combined in any suitable way, within the scope of the overall disclosure of this document.

There is thus provided metal working fluid decontamination apparatus 10. The apparatus 10 uses a combination of filtration and UV light treatment to decontaminate metal working fluids and reduces/eliminates the use of biocides. In comparison with conventional arrangements, costs are reduced, the health and safety risk is reduced and the working conditions of operatives are improved. The apparatus 10 is flexible in use to maximise energy efficiency. The reduction in use of biocides is a significant environmental benefit. The apparatus also reduces the frequency of disposal of the metal working fluid and hence operating cost, providing a further environmental benefit.

What is claimed is:

1. A method of decontaminating a metal working fluid comprising the steps of:
    providing a metal working fluid decontamination apparatus including:
        an intake arrangement for the metal working fluid;
        a pump for providing, in use, flow pressure to the metal working fluid;
        a decontaminator for reducing contamination in the metal working fluid;

an outlet arrangement for the metal working fluid;
    the decontaminator comprises a filter arrangement, to reduce particulate contamination in the metal working fluid, wherein the filter arrangement comprises a microbial filter for filtering microbial particulates such as bacteria, and, wherein, the microbial filter is at least a 1.0 micron filter,
    the decontaminator comprises an ultraviolet (UV) light treatment arrangement which comprises a UV light source, the UV light treatment arrangement defines a treatment passage;
    wherein, the metal working fluid is a fully synthetic metal working fluid comprising water and a water soluble synthetic concentrate which does not contain oil, and wherein the metal working fluid is substantially transparent and in a fresh unused condition,
operating the pump to draw the metal working fluid into the apparatus and provide flow pressure to move the metal working fluid through the apparatus to the outlet arrangement via the decontaminator; and
reducing contamination in the metal working fluid in the decontaminator including in flow sequence (i) filtering the metal working fluid in the filter arrangement to restore the transparency of the metal working fluid so that after filtration, the metal working fluid is substantially transparent, and (ii) treating the substantially transparent metal working fluid with UV light as it flows along the treatment passage of the UV light arrangement.

2. The method of claim 1, in which the metal working fluid comprises, in a fresh unused condition, no more than 10% by weight and no less than 2% by weight of the water soluble synthetic concentrate.

3. The method of claim 1, in which the filter arrangement comprises a coarse filter for filtering particulates and, wherein, the coarse filter may be at least a 20 micron filter, and may be no more than a 5 micron filter.

4. The method of claim 1, in which the filter arrangement comprises a fine filter for filtering particulates and, wherein, the fine filter may be at least a 20 micron filter, and may be no more than a 0.5 micron filter.

5. The method of claim 1, in which the microbial filter is positively charged.

6. The method of claim 1, in which the metal working fluid decontamination apparatus comprises pressure gauges located upstream and downstream of said filter arrangement to indicate a pressure drop over the filter arrangement and thereby whether the microbial filter of the filter arrangement needs replacing.

7. The method of claim 1, in which the UV light source operates at a wavelength of 185 to 400 nm.

8. The method of claim 1, in which the UV light treatment arrangement includes passage walling, which defines the treatment passage, wherein the passage walling may be substantially transparent, and wherein the UV light treatment arrangement may include a flow disrupter, which, in use, alters a flow of the metal working fluid along the treatment passage from laminar flow to turbulent flow.

9. The method of claim 1, in which wherein the UV light treatment arrangement includes passage walling with an outside and at least four UV light sources, arranged around the outside of the passage walling, and may be equally spaced around the outside of the passage walling.

10. The method of claim 1, in which the UV light treatment arrangement is arranged so that the UV light source is located within the treatment passage, so that, in use, the metal working fluid flows around the UV light source.

11. The method of claim 1, in which the metal working fluid decontamination apparatus includes a one or more pH monitors for monitoring a pH of the metal working fluid located upstream of and/or downstream of the decontaminator.

12. The method of claim 1, in which the metal working fluid decontamination apparatus includes a pH adjuster, for adjusting a pH of the metal working fluid, wherein the pH adjuster is located in flow sequence after the decontaminator, wherein the pH adjuster includes a pH monitor for monitoring the pH of the metal working fluid; a dosing pump for dosing a pH adjustment fluid into the metal working fluid to adjust the pH of the metal working fluid; and a controller for controlling an operation of the dosing pump in accordance with the monitored pH in comparison with a predetermined desired pH level.

13. The method of claim 12, in which the pH adjustment fluid comprises a pH raising fluid.

14. The method of claim 12, in which the predetermined desired pH level is in a range 8.6-9.1.

15. The method of claim 1, in which the decontaminator includes a bypass flow line, to permit the metal working fluid to bypass the UV light treatment arrangement, and a bypass control valve arrangement for switching flow of the metal working fluid between a treatment condition, in which the metal working fluid flows through the UV light treatment arrangement, and a bypass condition, in which the metal working fluid flows through the bypass flow line.

16. The method of claim 15, in which the decontaminator includes a pH monitor, for monitoring a pH of the metal working fluid, wherein the pH monitor is located upstream of the UV light treatment arrangement, the decontaminator includes a bypass controller which receives a pH signal from the pH monitor, the bypass controller sends control signals to the bypass control valve arrangement to switch the flow between the treatment condition and the bypass condition and the switching is dependent on the monitored pH at the pH monitor relative to a predetermined pH control value.

17. The method of claim 15, in which the decontaminator includes a pH monitor, for monitoring a pH of the metal working fluid, wherein the pH monitor is located upstream of the UV light treatment arrangement, the decontaminator includes a bypass controller which receives a pH signal from the pH monitor, the bypass controller sends control signals to the bypass control valve arrangement to switch the flow between the treatment condition and the bypass condition and the switching is dependent on the monitored pH at the pH monitor relative to a predetermined pH control value, and the predetermined pH control value is 8.5.

18. The method of claim 1, in which the metal working fluid does not comprise a bactericide.

19. The method of claim 1, in which the metal working fluid is for use as one or more of a cutting fluid, a grinding fluid, a drawing and/or forming fluid, a coolant, a component cleaner, a press lubricant, a corrosion inhibitor and/or a degreaser.

20. The method of claim 1, in which the metal working fluid comprises, in a fresh unused condition, no more than 7% by weight and no less than 5% by weight of the water soluble synthetic concentrate.

\* \* \* \* \*